US009116218B2

(12) United States Patent
Hurd

(10) Patent No.: US 9,116,218 B2
(45) Date of Patent: Aug. 25, 2015

(54) SYSTEM AND METHOD FOR TISSUE SPECIFIC MR IMAGING OF METABOLITES USING SPECTRAL-SPATIALLY FORMED STIMULATED ECHO

(75) Inventor: Ralph E. Hurd, Milpitas, CA (US)

(73) Assignee: General Electric Company, Schenectady, NY (US)

(*) Notice: Subject to any disclaimer, the term of this patent is extended or adjusted under 35 U.S.C. 154(b) by 326 days.

(21) Appl. No.: 12/844,876

(22) Filed: Jul. 28, 2010

(65) Prior Publication Data

US 2010/0283465 A1 Nov. 11, 2010

Related U.S. Application Data

(62) Division of application No. 12/022,622, filed on Jan. 30, 2008, now Pat. No. 7,772,844.

(51) Int. Cl.
*A61B 5/05* (2006.01)
*G01R 33/485* (2006.01)
*A61B 5/055* (2006.01)
(Continued)

(52) U.S. Cl.
CPC .............. *G01R 33/485* (2013.01); *A61B 5/055* (2013.01); *G01R 33/5601* (2013.01); *G01R 33/5617* (2013.01); *G01R 33/4833* (2013.01)

(58) Field of Classification Search
CPC .............. A61B 5/055; G01R 33/5617; G01R 33/5601; G01R 33/485; G01R 33/4833
USPC .......................................... 324/309; 600/414
See application file for complete search history.

(56) References Cited

U.S. PATENT DOCUMENTS 4,698,592 A * 10/1987 Feinberg ........................ 324/309
4,748,409 A *  5/1988 Frahm et al. ................... 324/309
(Continued)

FOREIGN PATENT DOCUMENTS

JP   05-204995 A    8/1993
JP   07-308307 A   11/1995
(Continued)

OTHER PUBLICATIONS

Ricci et al., Effect of Voxel Position on Single-Voxel MR Spectroscopy Findings, AJNR Am J Neuroradiol 21:367-374, Feb. 2000.*
(Continued)

*Primary Examiner* — Bo J Peng
(74) *Attorney, Agent, or Firm* — Ziolkowski Patent Solutions Group, SC

(57) ABSTRACT

A system for magnetic resonance (MR) spectroscopy includes a plurality of gradient coils positioned about a bore of a magnet and an RF coil assembly coupled to a pulse generator to emit RF pulse sequences and arranged to receive resulting MR signals from a subject of interest. A system control is also included in the MR spectroscopy system and is coupled to the plurality of gradient coils and the RF coil assembly. The system control is programmed to cause the RF coil assembly to emit a first RF pulse and a second RF pulse, wherein at least one of the first and second RF pulses is spectrally selective and at least one of the first and second RF pulses is spatially selective. The system control is also programmed to cause the RF coil assembly to emit a third RF pulse after a pre-defined time delay to generate a stimulated echo and detect MR signals resulting from the stimulated echo.

12 Claims, 8 Drawing Sheets

(51) Int. Cl.
*G01R 33/56* (2006.01)
*G01R 33/561* (2006.01)
*G01R 33/483* (2006.01)

(56) References Cited

U.S. PATENT DOCUMENTS

| | | | |
|---|---|---|---|
| 5,379,766 | A | 1/1995 | McKinnon et al. |
| 5,709,208 | A | 1/1998 | Posse et al. |
| 5,804,966 | A | 9/1998 | Hurd |
| 5,936,404 | A * | 8/1999 | Ladebeck et al. ............. 324/300 |
| 6,469,505 | B1 | 10/2002 | Maier et al. |
| 6,479,994 | B1 | 11/2002 | Hills et al. |
| 6,583,623 | B1 | 6/2003 | Kwok et al. |
| 6,704,594 | B1 | 3/2004 | Blank et al. |
| 6,791,323 | B2 | 9/2004 | Wang et al. |
| 6,900,634 | B2 * | 5/2005 | Roell ............................ 324/309 |
| 7,202,665 | B1 | 4/2007 | Reeder |
| 7,719,269 | B2 | 5/2010 | Petersson et al. |
| 2005/0070785 | A1 | 3/2005 | Ahluwalia et al. |

FOREIGN PATENT DOCUMENTS

| | | |
|---|---|---|
| JP | 2000-014657 A | 1/2000 |
| JP | 2001-231763 A | 8/2001 |
| JP | 2008-126069 A | 6/2008 |
| JP | 2010-099539 A | 5/2010 |

OTHER PUBLICATIONS

Aue, et al. Volume-Selective Excitation. A Novel Approach to Topical NMR, J. Mag. Res. 56, 350-354, 1984.*
Golman et al., Real-time metabolic imaging, PNAS, Jul. 25, 2006, vol. 103, No. 30, 11270-11275.*
Pfeuffer et al., Localized in Vivo 1H NMR Detection of Neurotransmitter Labeling in Rat Brain During Infusion of [1-13C] D-Glucose, Magnetic Resonance in Medicine 41:1077-1083, 1999.*
Burstein, Stimulated Echoes: Description, Applications, Practical Hints, Concepts in Magnetic Resonance, vol. 8 (4) 269-278, 1996.*
Haase Axel et al., "Multiple Chemical-Shift-Selective NMR Imaging Using Stimulated Echoes", Journal of Magnetic Resonance, Academic Press, London, GB, Part 64, No. 1, XP023960724, ISSN: 0022-2364, Aug. 1, 1985. pp. 94-102.
Nelson S. J. et al., "Hyperpolarized C-13 MRSI Data of Dog Prostrate at 3T", Proceedings of the International Society for Magnetic Resonance in Medicine, Joint Annual Meeting ISMRM-ESMRMB, XP002618378, Berlin, May 21, 2007, p. 536.
Thompson Richard B. et al., "Response of Metabolites With Coupled Spins to the STEAM Sequence", Magnetic Resonance in Medicine, Wiley, USA, Part 45, No. 6, XP002618647, ISSN: 0740-3194, Jun. 2001, pp. 955-965.
Search Report and Written Opinion issued in connection with corresponding NL Application No. NL2002411 on Jan. 26, 2011.
Unofficial translation of Japanese Office Action for JP Application No. 2009-008376, dated Aug. 13, 2013.

* cited by examiner

FIG. 3
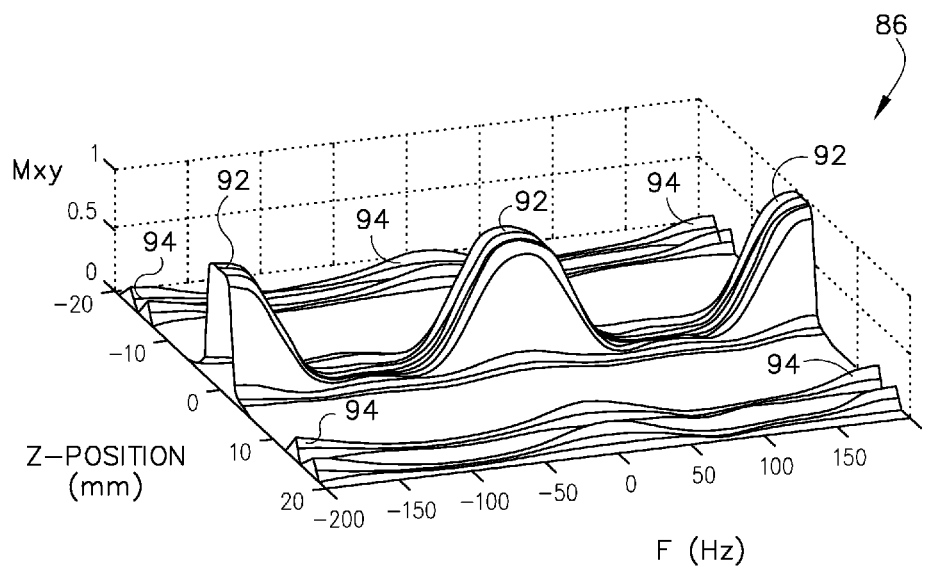
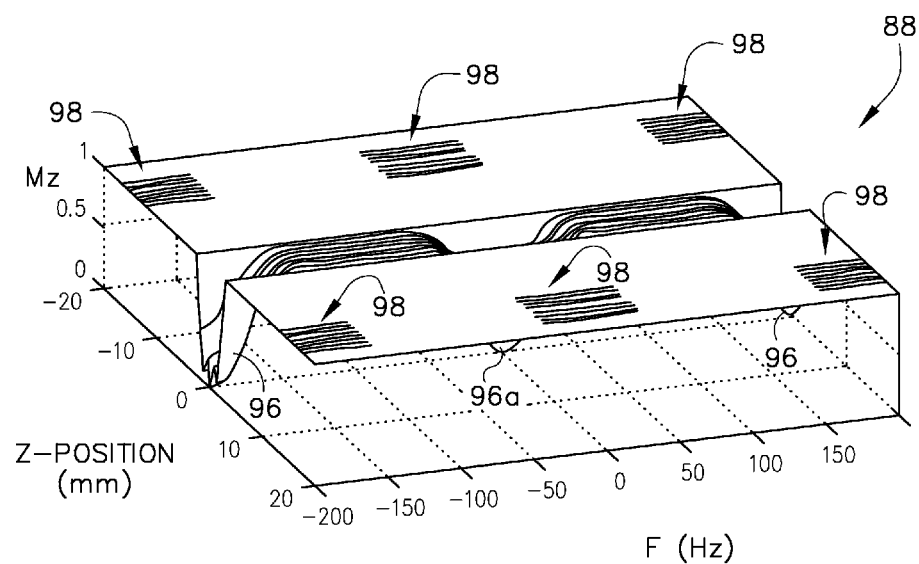

SYSTEM AND METHOD FOR TISSUE SPECIFIC MR IMAGING OF METABOLITES USING SPECTRAL-SPATIALLY FORMED STIMULATED ECHO

CROSS REFERENCE TO RELATED APPLICATIONS

The present application is a divisional of and claims priority to U.S. Ser. No. 12/022,622, now U.S. Pat. No. 7,772,844, filed on Jan. 30, 2008, the disclosure of which is incorporated herein.

BACKGROUND OF THE INVENTION

Embodiments of the invention relate generally to magnetic resonance (MR) imaging, and more particularly, to tissue-specific MR imaging of metabolites using spectral-spatially formed stimulated echoes.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which has a frequency near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The set of received nuclear magnetic resonance (NMR) signals resulting from a scan sequence are digitized and sent to a data processing unit for image reconstruction using one of many well known reconstruction techniques. It is desirable that the imaging process, from data acquisition to reconstruction, be performed as quickly as possible for improved patient comfort and throughput.

For some procedures and investigations, it is also desirable for MR images to display spectral information in addition to spatial information. The traditional method for creating such images is known as "chemical shift imaging" (CSI). CSI has been employed to monitor metabolic and other internal processes of patients, including imaging hyperpolarized substances such as 13C labeled contrast agents and metabolites thereof. In such 13C imaging, spectral composition is dependent not only on tissue type and health of that tissue, but also on the time the image is acquired relative to the injection of the hyperpolarized 13C agent. The hyperpolarization of contrast agents tends to have a very limited lifetime; typical T1 lifetimes are on the order of a few minutes in vivo.

While CSI, as a sequence for imaging hyperpolarized substances, provides valuable information on tissue type and health of that tissue, prior art CSI does not distinguish where or when metabolic products are formed in a 13C-hyperpolarized metabolic imaging acquisition. That is, while hyperpolarized 13C imaging of 13C-1-pyruvate and its' metabolic products lactate, alanine and bicarbonate can provide tissue-specific metabolic fingerprints (spectra), these fingerprints can be confounded by the local uptake of metabolic products not formed in the tissue of interest. For example, lactate in the blood stream formed by the heart or by red blood cells may be taken up by the tissue of interest, confounding the measurement of locally formed lactate.

It would therefore be desirable to have a system and method of MR imaging with spectral information and hyperpolarization that is able to separate systemic from local metabolic activity. Specifically, it would be desirable to excite and image hyperpolarized agents and metabolites thereof for a volume of interest, while effectively excluding metabolic products formed outside the volume of interest.

BRIEF DESCRIPTION OF THE INVENTION

In accordance with one aspect of the invention, a magnetic resonance (MR) spectroscopy system includes a plurality of gradient coils, an RF coil assembly, and a system control. The system control is programmed to cause the RF coil assembly to emit a first RF pulse and a second RF pulse, wherein at least one of the first and second RF pulses is spectrally selective and at least one of the first and second RF pulses is spatially selective. The system control is also programmed to cause the RF coil assembly to emit a third RF pulse after a pre-defined time delay to generate a stimulated echo and detect MR signals resulting from the stimulated echo.

In accordance with another aspect of the invention, a method for magnetic resonance (MR) imaging includes exciting a resonant frequency of a contrast agent, spatially limiting the excitation of the contrast agent to a slice or volume of interest, and detecting a first set of MR signals from the spatially limited excitation of the contrast agent. The method also includes, after a metabolic mixing time, exciting resonant frequencies for the contrast agent and at least one metabolic product formed from the contrast agent, detecting a second set of MR signals resulting from the excitation of the contrast agent and the at least one metabolic product after the metabolic mixing time, and generating a spectroscopic image from the detected first and second set of MR signals.

In accordance with yet another aspect of the invention, a computer readable storage medium includes a computer program stored thereon that represents a sequence of instructions that, when executed by a computer, causes the computer to request transmission of a spectral-spatial pulse at a first frequency and request transmission of a follow-up RF pulse, with the spectral-spatial pulse and the follow-up RF pulse generating a spin echo. The sequence of instructions also causes the computer to request transmission of at least one read RF pulse encompassing one or more frequencies, with the spectral-spatial pulse, the follow-up RF pulse, and the at least one read RF pulse generating a stimulated echo. The sequence of instructions further causes the computer to acquire magnetic resonance (MR) signals from the spin echo and the stimulated echo to generate a spectroscopic image and store the MR signals in computer memory.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings:

FIG. 3 is a 3-D graph of an excitation profile for a spectral-spatial pulse in accordance with an embodiment of the invention.

DETAILED DESCRIPTION OF THE PREFERRED EMBODIMENT

A system and method for slice-selectively exciting a resonant frequency for a metabolic reactant and for reading out a resulting metabolic process as a spectroscopic image is provided. In this regard, a pair of RF pulses may be emitted to spectral-spatially excite a frequency in a subject of interest for a specified metabolic reactant. Spectral-spatial radio frequency (RF) pulses may be used to create magnetization in a specific frequency profile without significantly affecting neighboring slices or nearby frequency ranges. A third RF pulse (either non-spectrally selective or spectrally selective) may then be emitted to generate a stimulated echo and excite a broad range of frequencies in the subject of interest for a plurality of metabolic products derived in vivo from the metabolic reactant. The signals resulting from these pulses are read in one or more of several well-known read out sequences.

Figure 1:
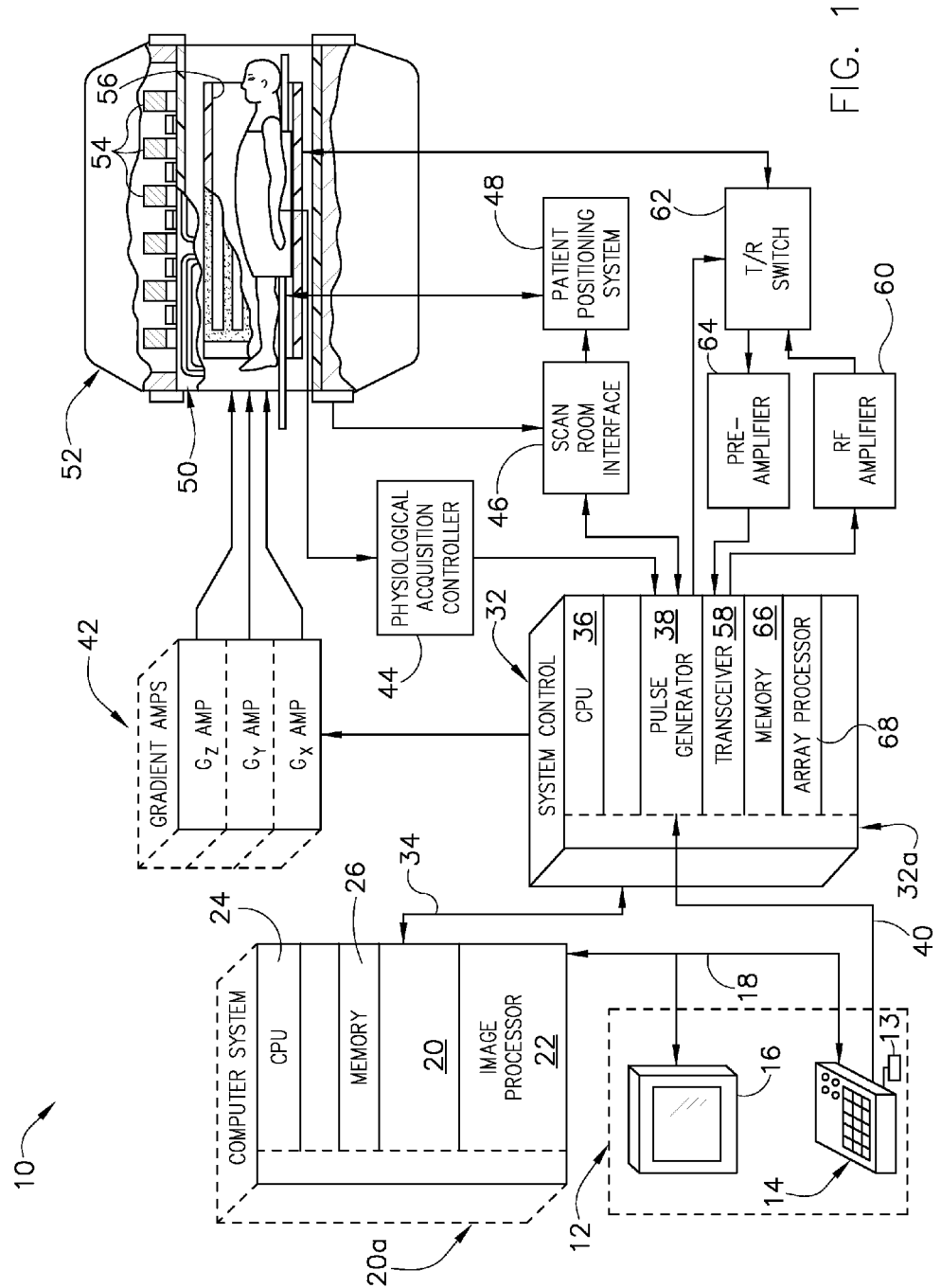
FIG. 1 is a schematic block diagram of an exemplary MR imaging system incorporating an embodiment of the invention.

Referring to FIG. 1, the major components of an exemplary magnetic resonance imaging (MRI) system 10 incorporating embodiments of the invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26 that may include a frame buffer for storing image data arrays. The computer system 20 is linked to archival media devices, permanent or back up memory or a network for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

Figure 2:
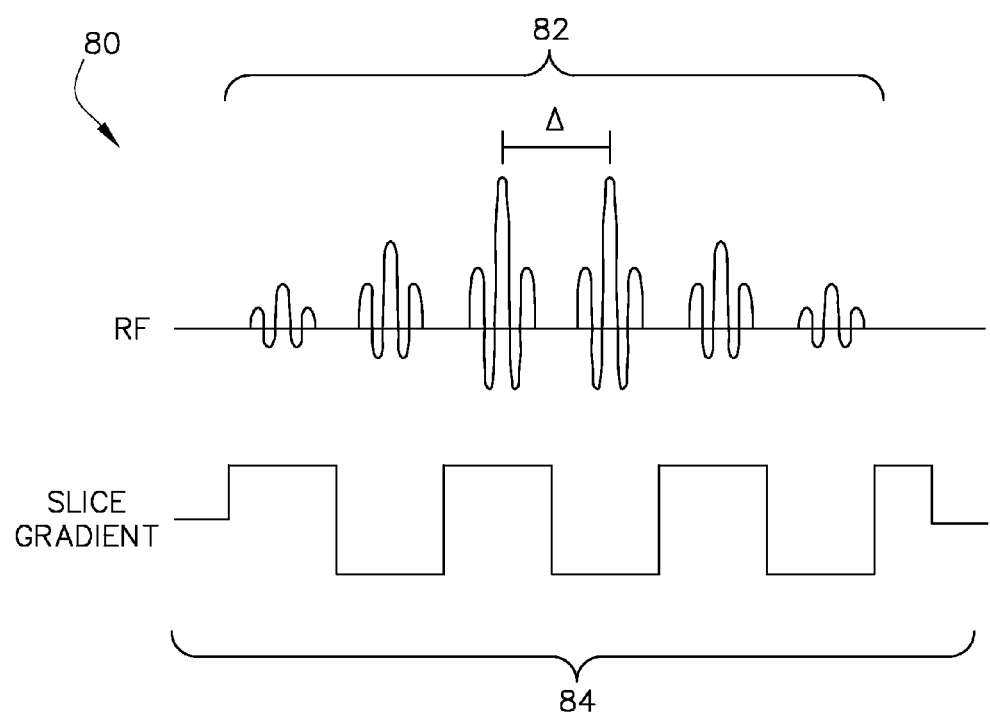
FIG. 2 is a graph of an exemplary RF pulse train and slice gradient waveform of a spectral-spatial pulse in accordance with an embodiment of the invention.

Referring now to FIG. 2, an exemplary spectral-spatial type excitation pulse 80 is depicted. As discussed above, spectral-spatial imaging is a type of imaging in which spectral data regarding the type of substance being imaged is combined with the typical slice selection of common MR imaging. Excitation pulse 80 includes a number of RF sub-elements 82. As shown, these RF sub-elements 82 represent periodic sin c functions of gradually increasing, then decreasing amplitudes. However, it is recognized that RF sub-elements 82 may take many forms other than merely sin c functions, such as Gaussian waveforms. The frequency of the RF sub-elements 82 may be selected to correspond to the resonant frequency of a particular substance of interest, for spectral encoding. For example, the resonant frequency of nuclei of a hyperpolarized substance may be targeted by pulse 80.

Along with the RF sub-elements 82, a slice encoding gradient 84 is applied. Slice encoding gradient 84 is a periodic gradient of alternating sign. In combination, RF sub-elements 82 and gradient 84 allow for slice-selective excitation within a specific frequency range. The spectral excitation profile of the pulse 80 (to be described below) is periodic with a periodicity of $1/\Delta$ Hz, where $\Delta$ represents the time distance between the sub-elements 82 of the RF waveform 80. In a preferred embodiment, excitation pulse 80 is applied to effect approximately a 90 degree total flip angle, though it is contemplated that other flip angles are also suitable. For example, the polarization and sensitivity to RF magnetization destruction of a contrast agent, the number of excitations desired, or the desired image resolution may affect the strength of the pulse to be applied.

Referring now to FIG. 3, the effects upon magnetization of an arbitrary spectral-spatial pulse (such as described with reference to FIG. 2) are shown. The upper plot 86 shows transverse magnetization Mxy and the lower plot 88 shows longitudinal magnetization Mz. The horizontal axes of the plots 86, 88 represent spectral frequency, the front-to-back axes represent geometric position along the z axis, and the vertical axes show magnetization. As shown, the primary transverse magnetization 92 is centered along the position marked as 0 mm along the z-position axis. Along the spectral axis, the magnetization 92 is periodic, centered at 0 Hz. As discussed above, the periodicity of magnetization 92 is dependant upon the $\Delta$ component of the spectral-spatial pulse applied. Thus, a desired period $1/\Delta$Hz may be attained by altering this characteristic of the spectral-spatial pulse. Magnetization 94 outside the primary slice is relatively weak in comparison. Likewise, magnetization at spectral positions 100 Hz on either side of primary magnetization 92 is nearly non-existent.

Lower plot 88 of FIG. 3 shows converse effects upon longitudinal magnetization. A corresponding primary decrease in longitudinal magnetization 96 is centered at the position marked as 0 mm along the z-position (front-to-back) axis. The primary reduction in magnetization 96 is periodic, centered at 0 Hz, as is the case with transverse magnetization. The period of the primary longitudinal magnetization reduction 96 is also $1/\Delta$Hz, dependant upon the spectral-spatial pulse applied. Magnetization at approximately 100 Hz on either side of primary magnetization reduction 96 remains at the initial strength (i.e. essentially unchanged by application of the spectral-spatial pulse). Likewise, magnetization 98 outside the primary slice along the z-position axis remains relatively unchanged.

Figure 4:
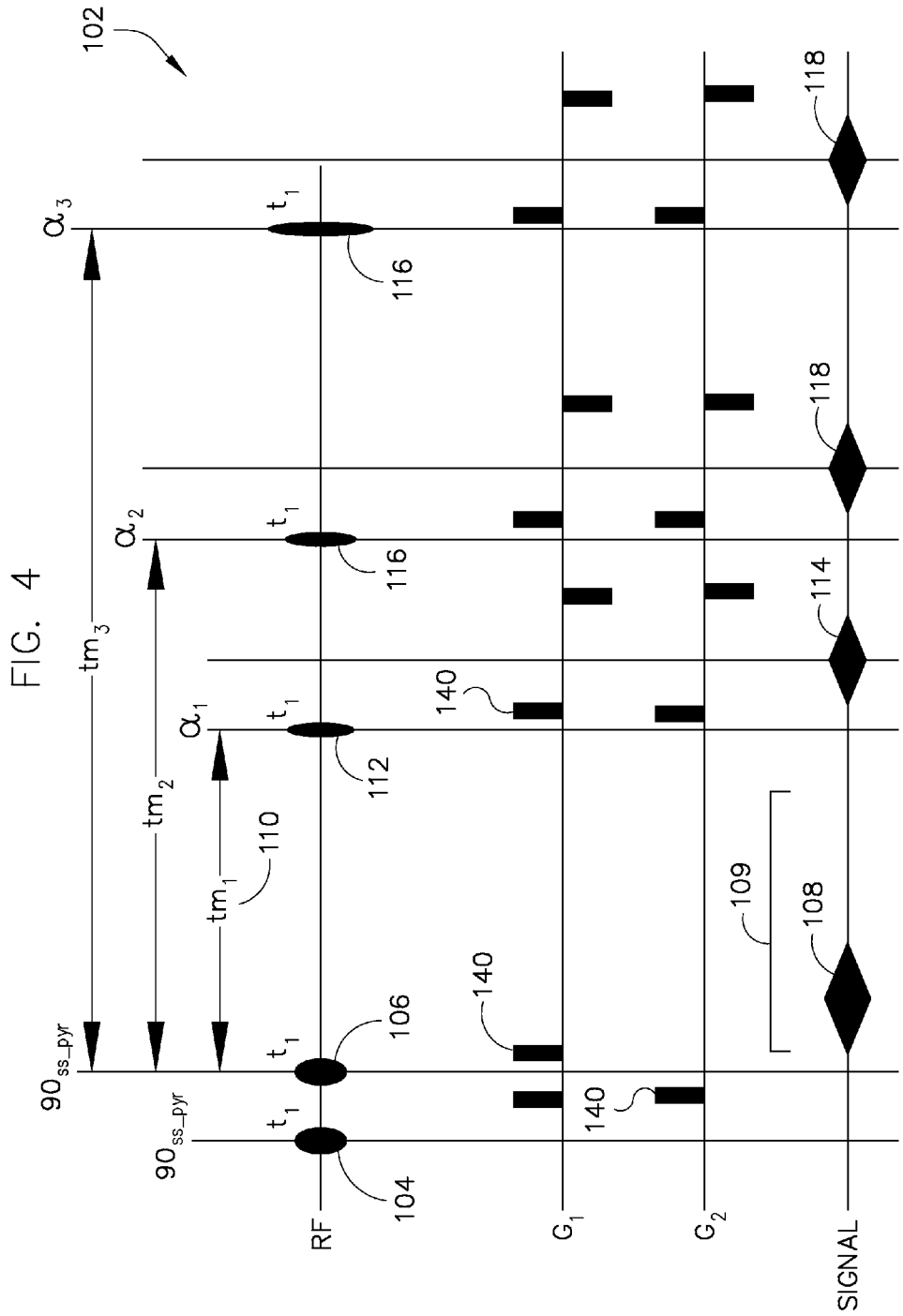
FIG. 4 is a diagram of an imaging sequence in accordance with an embodiment of the invention.

Referring now to FIG. 4, one embodiment of a data acquisition sequence 102 incorporating spectral-spatial pulses 104, 106, as described above, is shown. In a preferred embodiment, sequence 102 is adapted for imaging a metabolic process. In this regard, the excitation frequency of the spectral-spatial pulses 104, 106 may be keyed to the resonant frequency of a hyperpolarized contrast agent (i.e., metabolic reactant). For example, the excitation frequency of spectral spatial pulses 104, 106 may be designed to excite the nuclei of hyperpolarized 13C labeled pyruvate. However, it is recognized that other substances with other excitable nuclei are equally applicable (such as other 13C-enriched compounds or substances having 15-N, 31-P, 19-F, 29-Si, 129-Xe nuclei, and other NMR relevant nuclei).

Acquisition sequence 102 begins with emission of a first spectral-spatial pulse 104, which causes excitation of a substance of corresponding resonant frequency. A second spectral-spatial pulse 106 (i.e., a follow-up RF pulse) is then transmitted at the same frequency as the first spectral-spatial pulse 104. Second spectral-spatial pulse 106 is preferably applied at a time midway between the application of the first spectral-spatial pulse 104 and the peak of a spin echo 108. (i.e., one-half the echo time (TE), TE/2) Preferably, spectral-spatial pulses 104, 106 have flip angles of approximately 90 degrees. As shown in FIG. 4, the combination of the first and second spectral-spatial pulses 104, 106 produces a spin echo 108 (i.e., Hahn echo). A read-out or data sampling/acquisition stage 109 begins after application of second spectral-spatial pulse 106, and signals from spin echo 108 are sampled or otherwise acquired (i.e., a first set of MR signals are acquired). Read-out may take the form of several well-known acquisition sequences, such as an echo planar imaging (EPI) readout (for example, spin echo EPI), a rapid acquisition with relaxation enhancement (RARE) readout, a true fast imaging with steady precession (trueFISP) readout, or variations thereof. The MR signals acquired from the spin echo comprises signals from the excited substance (e.g., 13-C labeled pyruvate) and is limited to a slice or volume of interest.

Upon acquisition of the spectrally and spatially limited signals from the spin echo 108, the acquisition sequence 102 delays for a remainder of a pre-defined delay period 110, the length of which is measured from the application of the second spectral-spatial pulse 106. While the pre-defined delay period 110 is shown in FIG. 4 as being measured from after the application of the second spectral-spatial pulse 106, it is also recognized that the pre-defined delay period 110 could be a time period measured from introduction of the hyperpolarized contrast agent into the patient. The pre-defined delay period 110 comprises a metabolic mixing time $Tm_1$ that allows for sufficient metabolization of the hyperpolarized contrast agent to occur. That is, metabolic mixing time $Tm_1$ allows for metabolization of the hyperpolarized contrast agent into a plurality of metabolic products. These metabolic products can include, but are not limited to, lactate, alanine, and bicarbonate. The length of the metabolic mixing time $Tm_1$ can be selected by a system operator and can extend over several T1 decay periods (e.g., 3 T1 periods), being limited only by the length of time the contrast agent remains in a hyperpolarized state.

After the metabolic mixing time $Tm_1$ has passed, a third RF pulse 112 (i.e., a read pulse) is applied to excite a desired number of frequencies. In one embodiment, the third RF pulse 112 is a non-spectrally selective read RF pulse designed to cause the excitation of the resonant frequency for the hyperpolarized contrast agent as well as the resonant frequencies of each of the metabolic products. In another embodiment, however, third RF pulse 112 is a spectrally selective pulse designed to be spectrally selective for a specific metabolic product. Upon application of the third RF pulse 112, a stimulated echo 114 is formed from which a second set of MR signals is sampled or otherwise acquired. More specifically, the combination of the first spectral spatial pulse 104, the second spectral-spatial pulse 106, and the third RF pulse 112 generates the stimulated echo 114. Depending on the spectral selectivity (i.e., whether the third RF pulse is spectrally selective or non-spectrally selective) of the third RF pulse 112 that is applied, the signals contained in the stimulated echo 114 can include signals from the original hyperpolarized contrast agent, a specified metabolic product, or the hyperpolarized contrast agent and a plurality of the metabolic products formed during the metabolic mixing time $Tm_1$.

As shown in FIG. 4, it is envisioned that additional spectrally selective or non-spectrally selective read RF pulses 116 can also be applied in the acquisition sequence 102. That is, signals for the original hyperpolarized contrast agent and/or signals from one or more of the metabolic products can be acquired at additional, varied metabolic mixing times (Tm2, Tm3 . . . ) by way of additional stimulated echoes 118. Thus, the metabolization of the hyperpolarized contrast agent and the formation of metabolic products can be measured at varying points in the T1 decay periods of the excited hyperpolarized contrast agent (i.e., over the several T1 decay periods of the excited hyperpolarized contrast agent). To maintain signal strength in each of the stimulated echoes 114, 118 that are formed from the one or more read RF pulses 112, 116, the read RF pulses 112, 116 can have low flip angles (a), such as, for example, 15 degrees. The low flip angle pulses allow for a plurality of stimulated echoes 114, 118 to be generated and allow for signals to be acquired from each of those stimulated echoes 114, 118. The number of additional read RF pulses 116 that can be applied in the acquisition sequence 102 is limited only by the longitudinal relaxation time of the excited hyperpolarized contrast agent.

As shown in FIG. 4, gradient pulses 140 are also applied during the acquisition sequence 102, 120 as G1 and G2 gradients. Gradients G1, G2 correspond to gradients applied along a pair of arbitrary axes (e.g., orthogonal axes) and the gradient pulses 140 are crusher gradients that function to spoil spin echo responses and rephase stimulated echo responses. It is envisioned that varying gradients G1, G2 can be applied to correspond with the data acquisition desired from a specified acquisition sequence and that gradient pulse patterns are not limited to those shown in FIG. 4.

Figure 5:
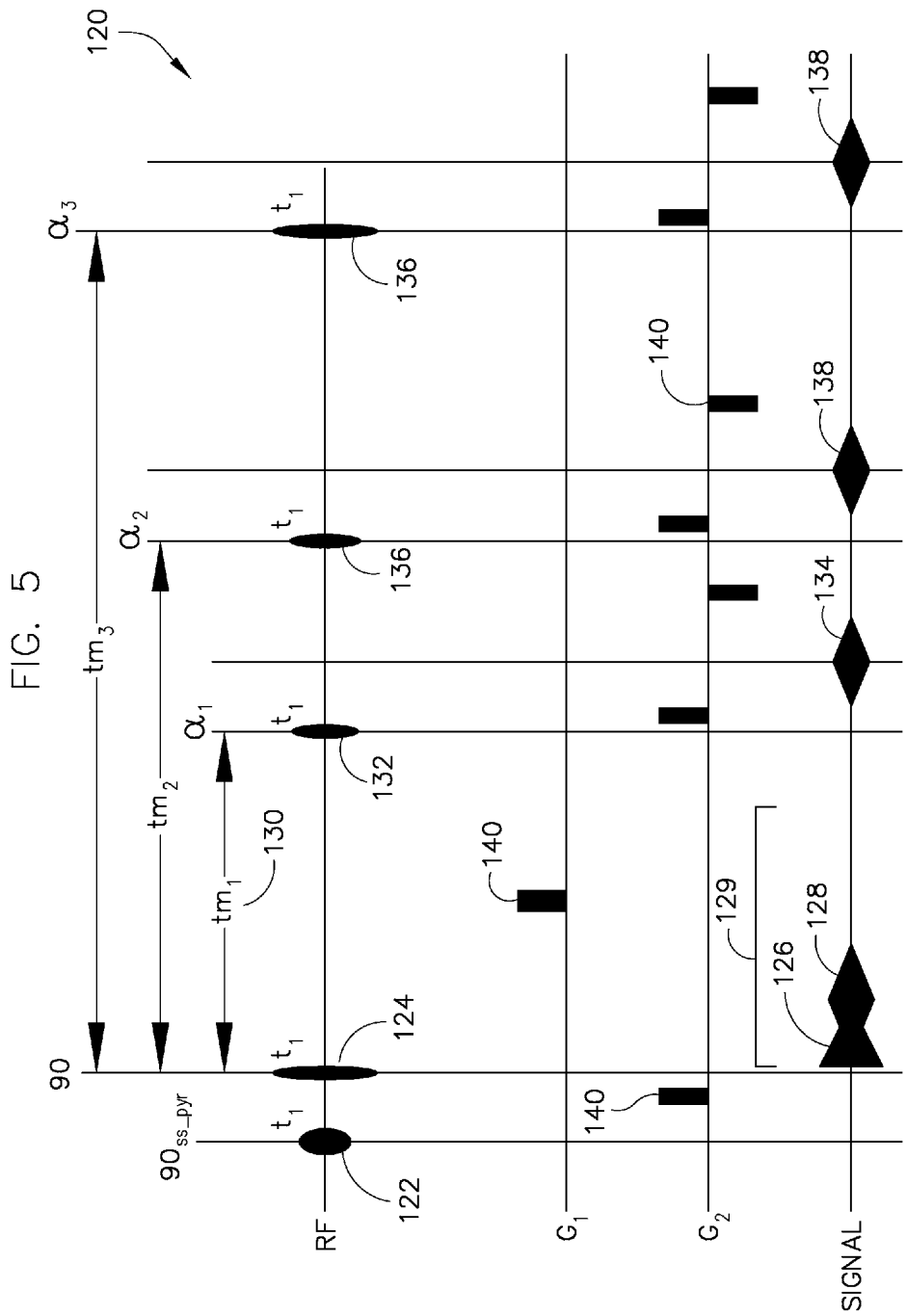
FIG. 5 is a diagram of an imaging sequence in accordance with another embodiment of the invention.

Referring now to FIG. 5, another embodiment of a data acquisition sequence 120 incorporating a spectral-spatial pulse 122 is shown. In the embodiment of FIG. 5, acquisition sequence 120 begins with emission of a spectral-spatial pulse 122, which causes excitation of a hyperpolarized contrast agent of corresponding resonant frequency. A follow-up RF pulse 124 is then transmitted in the form of a non-spectrally selective RF pulse. The follow-up RF pulse 124 causes excitation for a number of metabolic products that begin to form after in-vivo introduction of the hyperpolarized contrast agent. Preferably, spectral-spatial pulse 122 and follow-up RF pulse 124 have flip angles of approximately 90 degrees, and, preferably, follow-up RF pulse 124 is applied at a time of TE/2 after spectral-spatial pulse 122. From the first spectral-spatial pulse 122 and the follow-up RF pulse 124, free induction decay (FID) signals 126 and a spin echo signal 128 are generated. Specifically, the non-spectrally selective follow-up RF pulse 124 generates FID signals 126 for the hyperpolarized contrast agent as well as for each of the metabolic products that are formed from metabolization of the hyperpolarized contrast agent. The combination of the spectral-spatial pulse 122 and the follow-up RF pulse 124 generates spin echo (i.e., Hahn echo) signals 128 from only the hyperpolarized contrast agent. A read-out or data sampling/acquisition stage 129 begins after emission of the follow-up RF pulse 124 to acquire the FID signals 126 and the spin echo signals 128, and the FID and spin echo signals 126, 128 are sampled or otherwise acquired during the read-out or data sampling/acquisition stage 129.

Referring still to FIG. 5, upon acquisition of the spectrally and spatially limited signals from the spin echo 128 and from the FID signals 126, the acquisition sequence 120 allows for remainder of a pre-defined delay period 130 (i.e., metabolic mixing time $Tm_1$) to pass. The metabolic mixing time $Tm_1$ allows for sufficient metabolization of the hyperpolarized contrast agent to occur, such that a plurality of metabolic products are formed, such as lactate, alanine, and bicarbonate.

After the metabolic mixing time $Tm_1$ has passed, a spectrally selective or a non-spectrally selective read RF pulse 132 is applied to excite a plurality of frequencies. The read RF pulse 132 can be designed to cause excitation of the resonant frequency for a specified metabolic product or of the resonant frequency for the hyperpolarized contrast agent as well as each of the metabolic products. Upon application of the read RF pulse 132, a stimulated echo 134 is formed. The signals contained in the stimulated echo 134 can include signals for the original hyperpolarized contrast agent along with signals from one or more of the metabolic products formed during the metabolic mixing time $Tm_1$.

As shown in FIG. 5, it is envisioned that additional read RF pulses 136 can also be applied in the acquisition sequence 120. That is, signals for the original hyperpolarized contrast agent and/or signals from one or more of the metabolic products can be acquired at additional metabolic mixing times ($Tm_2$, $Tm_3$ . . . ) by way of additional stimulated echoes 138. Thus, the metabolization of the hyperpolarized contrast agent, and the formation of metabolic products, can be measured at varying points in the T1 decay periods.

As shown in FIG. 5, gradient pulses 140 are applied during the acquisition sequence 102, 120 as G1 and G2 gradients and correspond to gradients applied along a pair of arbitrary axes (e.g., orthogonal axes). The gradient pulses 140 are crusher gradients that function to spoil FID and/or spin echo responses and rephase stimulated echo responses. It is envisioned that varying gradients G1, G2 can be applied to correspond with the data acquisition desired from a specified acquisition sequence and that gradient pulse patterns are not limited to those shown in FIG. 5.

Figure 6:
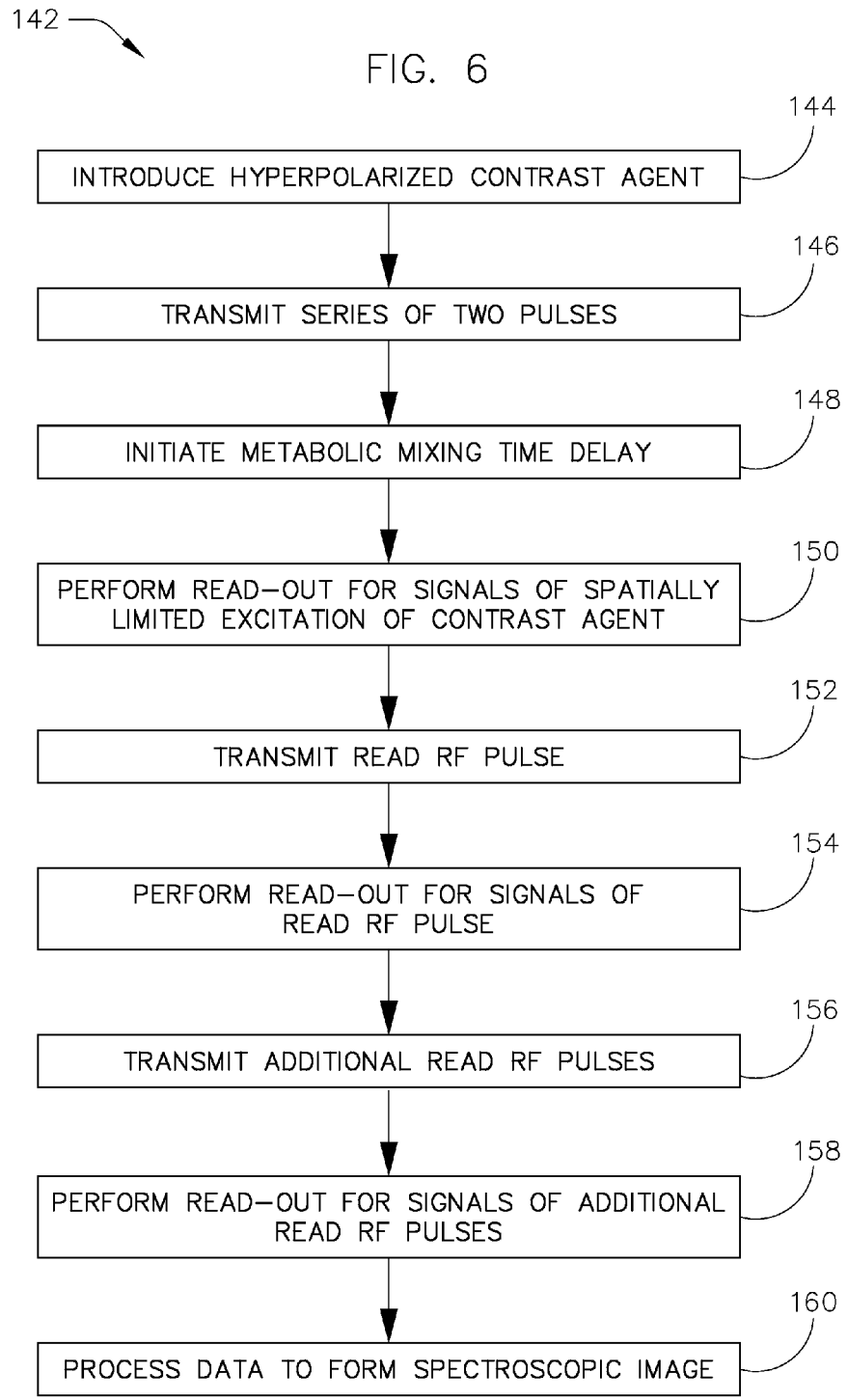
FIG. 6 is a flowchart illustrating a technique for MR imaging of metabolites at selective excitation frequencies in accordance with an embodiment of the invention.

FIG. 6 is a flowchart illustrating a technique 142 for spectroscopic imaging of a hyperpolarized contrast agent and its metabolic products in accordance with an embodiment of the invention. A hyperpolarized contrast agent is introduced into an imaging subject at block 144. Next, a series of two RF pulses are transmitted at block 146. The series of two RF pulses may be delayed a specific time period after introduction of the agent to allow for perfusion into tissues, or for the agent to reach an organ of diagnostic interest. At least one of the two RF pulses is transmitted at the resonant frequency of the contrast agent to induce excitation of the contrast agent and at least one of the two RF pulses is transmitted along with a slice selective gradient to form a spectral-spatial pulse that limits the excitation to a slice or volume of interest. At block 148, a metabolic mixing time delay is initiated upon the application of the second of the series of two RF pulses. Once excitation is complete, a signal read-out then begins at block 150 during which MR data is acquired from spin echo signals resulting from the series of two RF pulses, the signals being limited to the excited hyperpolarized contrast agent. Also, in one embodiment, the MR data additionally includes FID signals resulting from the series of two RF pulses when one of those pulses is non-spectrally selective.

Technique 142 continues by waiting a remainder of the metabolic mixing time delay that is initiated at block 148 during application of the second of the series of two RF pulses. The metabolic mixing time delay allows for the hyperpolarized contrast agent to metabolize in the patient and form metabolic products. Upon completion of the metabolic mixing time delay, a read RF pulse (spectrally or non-spectrally selective) is applied at block 152 to excite the resonant frequencies of the hyperpolarized contrast agent and/or one or more of the metabolic products. Once excitation is complete, a signal read-out then begins at block 154 during which MR data is acquired from a stimulated echo that is formed from the application of the read RF pulse (e.g., a spectrally or non-spectrally selective pulse). The MR data includes signals from the hyperpolarized contrast agent and/or one or more of the metabolic products. One or more additional read RF pulses can be applied at block 156 (spectrally or non-spectrally selective), with each pulse generating an additional stimulated echo signal that is read at block 158. Once all MR data has been acquired, the data is processed to perform spatial mapping or reconstruct a spectroscopic image, according to any of the known reconstruction techniques at block 160.

It is recognized that the application of technique 142 is not limited to a specific type of spatial mapping. For example, technique 142 could be used in a single voxel mode such as STEAM, where the sequence of three RF pulses (described in detail above) are used with orthogonal gradients to select a metabolic volume of interest, with no further spatial mapping. Technique 142, however, is also applicable to other spatially limited and non-spatially limited spectroscopic imaging techniques.

Figure 7:
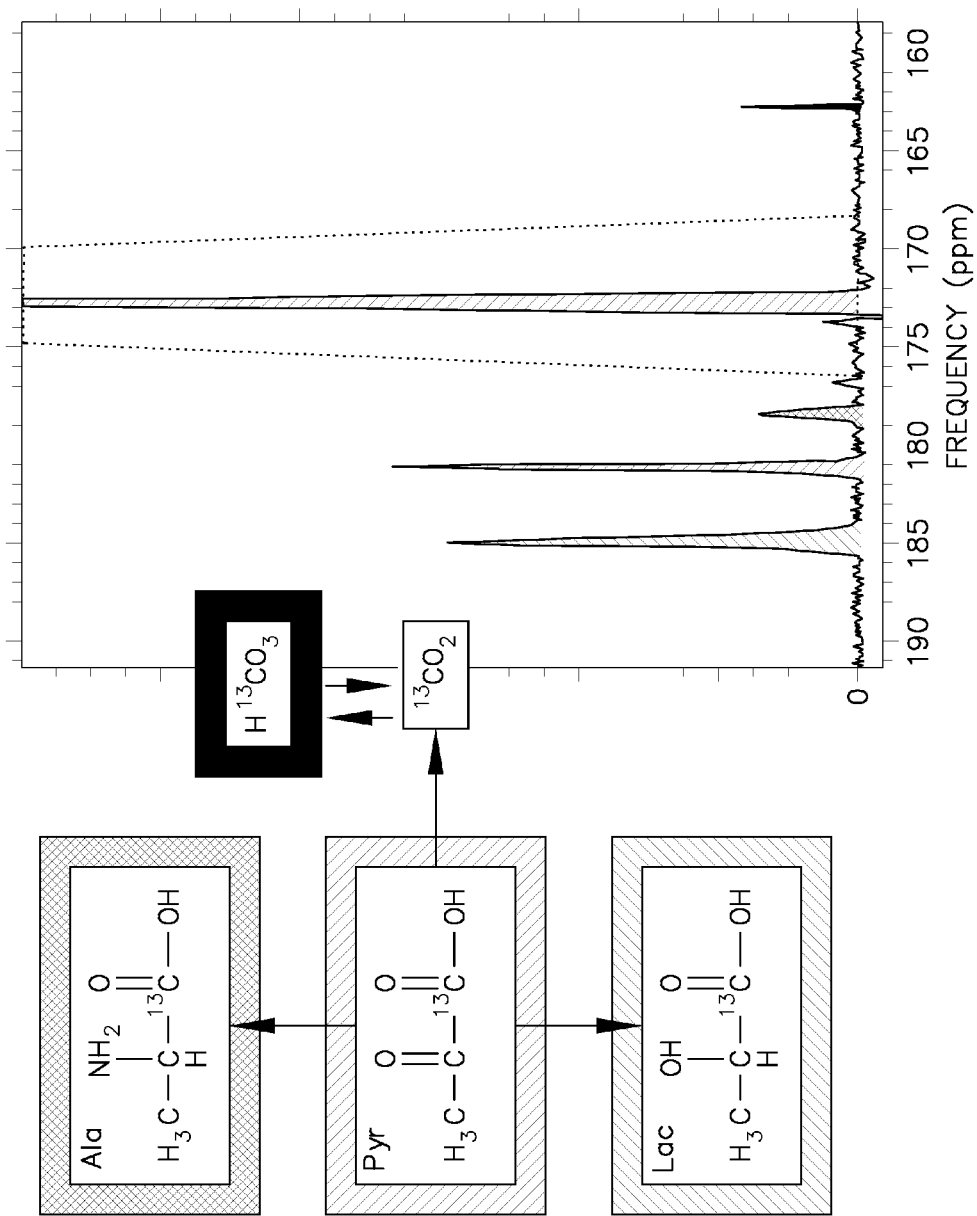
FIG. 7 is a 2-D graph of the spectral separation of 13C-1-pyruvate and its metabolic products, in accordance with an embodiment of the invention.

Referring now to FIG. 7, the spectral separation of 13C-1-pyruvate and its metabolic products at 3T is shown. As shown therein, selective excitation for the 13C-1-pyruvate is achieved by a spectrally limited RF excitation pulse. Signals from the 13C-1-pyruvate and the metabolic products can be acquired from the technique illustrated in FIG. 6.

Figure 8:
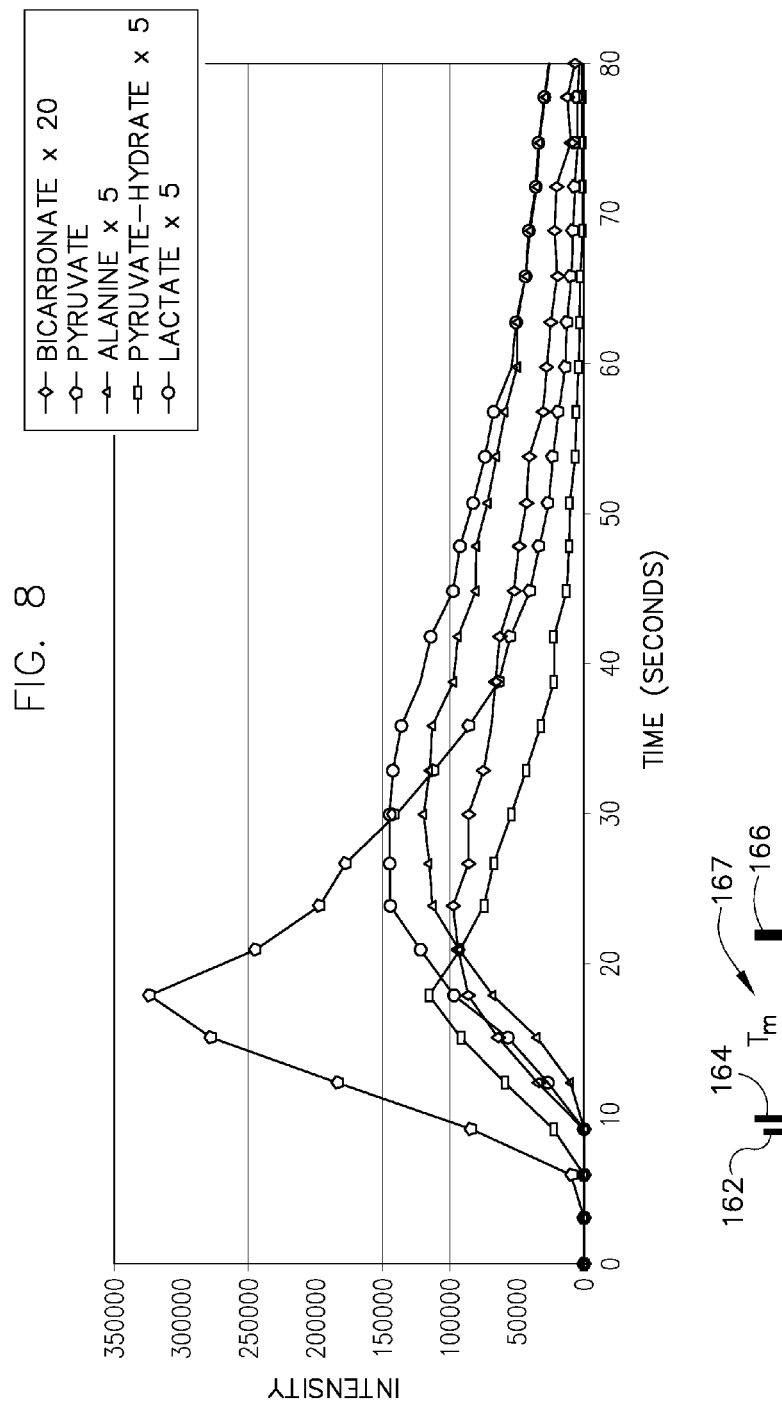
FIG. 8 is a graph of metabolic behavior of 13C-1-pyruvate relative to the timing of an exemplary spectral-spatial stimulated echo imaging sequence in accordance with an embodiment of the invention.

FIG. 8 displays the dynamic and metabolic behavior of 13C-1-pyruvate, and its metabolization into metabolic products, relative to the timing of the application of a spectral-spatial stimulated echo sequence, such as the pulse sequences set forth in FIGS. 4 and 5. In the embodiment shown of an exemplary pulse sequence shown in FIG. 8, a series of two RF pulses 162, 164 are transmitted. At least one of the two RF pulses is transmitted at the resonant frequency of the contrast agent (i.e., 13C-1-pyruvate) to induce excitation of the contrast agent and at least one of the two RF pulses is transmitted along with a slice selective gradient to form a spectral-spatial pulse that limits the excitation to a slice or volume of interest. As shown, the series of two RF pulses 162, 164 are separated by a time TE/2, which is one-half the time between the application of the first RF pulse 162 and the peak of a spin echo (not shown) generated by the series of the two RF pulses 162, 164. As further illustrated in FIG. 8, application of a non-spectrally selective RF pulse 166 for generating a stimulated echo does not occur until after a pre-determined delay period 167 (i.e., a metabolic mixing time, Tm) has passed during which the 13C-1-pyruvate is allowed to metabolize to a sufficient extent. Spectroscopic image acquisition 168 can then be achieved by way of readout of the stimulated echo generated by the third RF pulse 166.

A technical contribution for the disclosed method and apparatus is that is provides for a computer implemented tissue-specific MR imaging of metabolites using spectral-spatially formed stimulated echoes. Spectral-spatial radio frequency (RF) pulses are used to create magnetization in a specific frequency profile without significantly affecting neighboring slices or nearby frequency ranges. A spectrally or non-spectrally selective RF pulse is then used to generate a stimulated echo to create magnetization over a broad frequency profile, allowing for a metabolic process to be read out as a spectroscopic image.

Therefore, according to one embodiment of the invention, a magnetic resonance (MR) spectroscopy system includes a plurality of gradient coils, an RF coil assembly, and a system control. The system control is programmed to cause the RF coil assembly to emit a first RF pulse and a second RF pulse, wherein at least one of the first and second RF pulses is spectrally selective and at least one of the first and second RF pulses is spatially selective. The system control is also programmed to cause the RF coil assembly to emit a third RF pulse after a pre-defined time delay to generate a stimulated echo and detect MR signals resulting from the stimulated echo.

According to another embodiment of the invention, a method for magnetic resonance (MR) imaging includes exciting a resonant frequency of a contrast agent, spatially limiting the excitation of the contrast agent to a slice or volume of interest, and detecting a first set of MR signals from the spatially limited excitation of the contrast agent. The method also includes, after a metabolic mixing time, exciting resonant frequencies for the contrast agent and at least one metabolic product formed from the contrast agent, detecting a second set of MR signals resulting from the excitation of the contrast agent and the at least one metabolic product after the metabolic mixing time, and generating a spectroscopic image from the detected first and second set of MR signals.

According to yet another embodiment of the invention, a computer readable storage medium includes a computer program stored thereon that represents a sequence of instructions that, when executed by a computer, causes the computer to request transmission of a spectral-spatial pulse at a first frequency and request transmission of a follow-up RF pulse, with the spectral-spatial pulse and the follow-up RF pulse generating a spin echo. The sequence of instructions also causes the computer to request transmission of at least one read RF pulse encompassing one or more frequencies, with the spectral-spatial pulse, the follow-up RF pulse, and the at least one read RF pulse generating a stimulated echo. The sequence of instructions further causes the computer to acquire magnetic resonance (MR) signals from the spin echo and the stimulated echo to generate a spectroscopic image and store the MR signals in computer memory.

The invention has been described in terms of the preferred embodiments, and it is recognized that equivalents, alternatives, and modifications, aside from those expressly stated, are possible and within the scope of the appending claims. The order and sequence of process or method steps may be varied or re-sequenced according to alternative embodiments.

What is claimed is:

1. A method for magnetic resonance (MR) imaging comprising:
    exciting a resonant frequency of a contrast agent by transmitting a first RF pulse and a second RF pulse, and wherein at least one of the first RF pulse and the second RF pulse is spectrally limiting;
    spatially limiting the excitation of the contrast agent to a slice or volume of interest;
    detecting a first set of MR signals from the spatially limited excitation of the contrast agent;
    after a metabolic mixing time, exciting resonant frequencies for the contrast agent and at least one metabolic product formed from the contrast agent by transmitting at least one non-spectrally selective RF pulse after the metabolic mixing time;
    detecting a second set of MR signals resulting from the excitation of the contrast agent and the at least one metabolic product after the metabolic mixing time, wherein detecting the second set of MR signals comprises detecting stimulated echoes generated by the first and second RF pulses and the at least one non-spectrally selective RF pulse; and
    generating a spectroscopic image from the detected first and second set of MR signals;

wherein the detected second set of MR signals excludes signals from metabolic products formed outside the slice or volume of interest, so as to separate systemic metabolic activity from local metabolic activity in the slice or volume of interest.

2. The method of claim 1 wherein detecting the first set of MR signals comprises detecting at least one of a free induction decay (FID) signal and a spin echo signal generated by the first and second RF pulses.

3. The method of claim 1 wherein the at least one non-spectrally selective RF pulse is a low flip angle pulse having a flip angle of 15 degrees.

4. The method of claim 1 wherein the metabolic mixing time is measured from the emission of the second RF pulse, the metabolic mixing time designed to allow the metabolic product to metabolize into a plurality of metabolic products.

5. The method of claim 4 wherein the metabolic mixing time extends over a plurality of T1 time periods of the contrast agent.

6. The method of claim 1 further comprising emitting additional non-spectrally selective RF pulses after additional time delays subsequent to the metabolic mixing time, the additional non-spectrally selective RF pulses generating additional stimulated echoes.

7. The method of claim 6 wherein the each of the additional non-spectrally selective RF pulses comprises a low flip angle pulse having a flip angle of 15 degrees, so as to maintain signal strength in the additional stimulated echoes.

8. A method for magnetic resonance (MR) imaging comprising:
transmitting a first RF pulse and a follow-up RF pulse to generate a spin echo, wherein each of the first RF pulse and the follow-up RF pulse comprises a spectrally and spatially selective pulse designed to excite a hyperpolarized contrast agent at a specified frequency;
transmitting at least one read RF pulse that, in combination with the first RF pulse and the follow-up RF pulse, generate a stimulated echo, wherein the at least one read RF pulse comprises a spectrally selective read RF pulse designed to excite a specific metabolic product formed from metabolization of the hyperpolarized contrast agent during a metabolic mixing time;
acquiring magnetic resonance (MR) signals from the spin echo and the stimulated echo for a tissue or organ of interest while excluding metabolic products formed in neighboring tissues or organs, such that any effect of a local uptake of metabolic products not formed in the tissue of interest is excluded from the acquired MR signals; and
generating a spectroscopic image from the acquired MR signals.

9. The method of claim 8 wherein the hyperpolarized contrast agent comprises 13C-1-pyruvate.

10. The method of claim 8 wherein the at least one read RF pulse comprises a plurality of read RF pulses configured to generate a plurality of stimulated echoes.

11. The method of claim 10 wherein the plurality of read RF pulses are applied at varied metabolic mixing times of the hyperpolarized contrast agent, so as to enable measurement of the metabolization of the hyperpolarized contrast agent at varying points in T1 decay periods thereof.

12. The method of claim 10 wherein each of the plurality of read RF pulses comprises a low flip angle pulse having a flip angle of 15 degrees, so as to maintain signal strength in the plurality of stimulated echoes.

* * * * *